United States Patent [19]

Herum

[11] Patent Number: 5,436,053
[45] Date of Patent: * Jul. 25, 1995

[54] MEDICAL SHEET AND METHOD OF MANUFACTURE

[75] Inventor: Timothy D. Herum, Red Oak, Tex.

[73] Assignee: Bio Tex Ltd., Inc., DeSoto, Tex.

[ * ] Notice: The portion of the term of this patent subsequent to Apr. 12, 2011 has been disclaimed.

[21] Appl. No.: 44,803

[22] Filed: Apr. 12, 1993

Related U.S. Application Data

[62] Division of Ser. No. 667,424, Mar. 11, 1991, Pat. No. 5,227,218.

[51] Int. Cl.⁶ .............................................. B32B 3/04
[52] U.S. Cl. .................................. 428/128; 150/158; 428/296
[58] Field of Search .............. 428/102, 128, 130, 219, 428/194, 296; 150/158

[56] References Cited

U.S. PATENT DOCUMENTS

| | | | |
|---|---|---|---|
| 2,963,715 | 12/1960 | Young | 5/334 |
| 3,956,782 | 5/1976 | Morrison | 206/390 |
| 4,013,816 | 3/1977 | Sabee et al. | 428/288 |
| 4,196,245 | 4/1980 | Kitson et al. | 428/198 |
| 4,835,029 | 5/1989 | Thebaud et al. | 428/127 |
| 5,042,098 | 8/1991 | Stultz | 5/497 |
| 5,227,218 | 7/1993 | Herum | 428/102 |
| 5,252,374 | 10/1993 | Larsonneur | 428/77 |

Primary Examiner—Alexander S. Thomas
Attorney, Agent, or Firm—Harris, Tucker & Hardin; George R. Schultz

[57] ABSTRACT

A cover sheet for medical tables, beds or gurneys comprises a sheet formed from a high tensile strength, plastic with opposed ends of the sheet folded and seamed to provide pockets. The pockets are inverted for assemblage over the ends of the medical tables, beds or gurneys. Methods of continuously fabricating such cover sheets from a roll of plastic material are also disclosed.

2 Claims, 3 Drawing Sheets

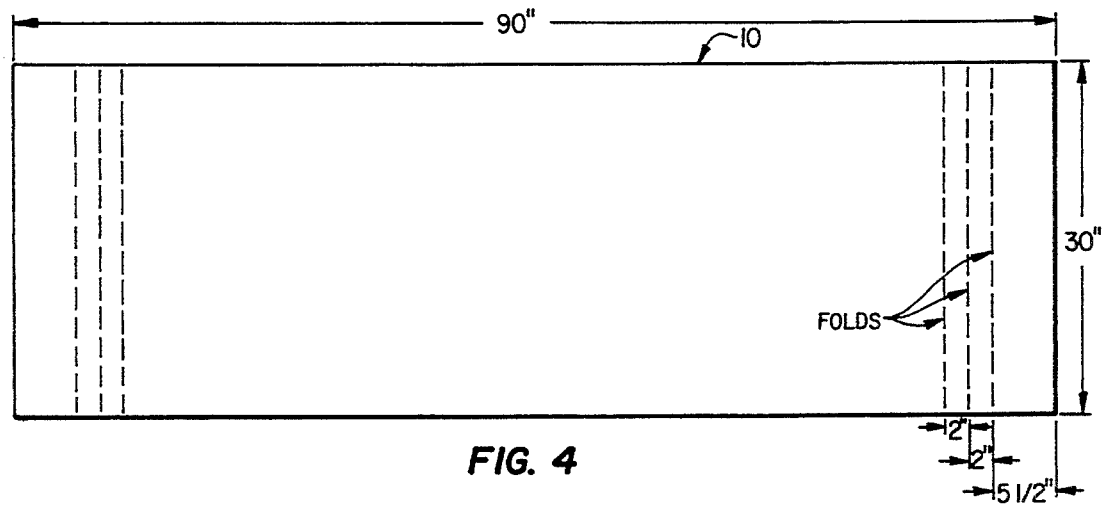
FIG. 4
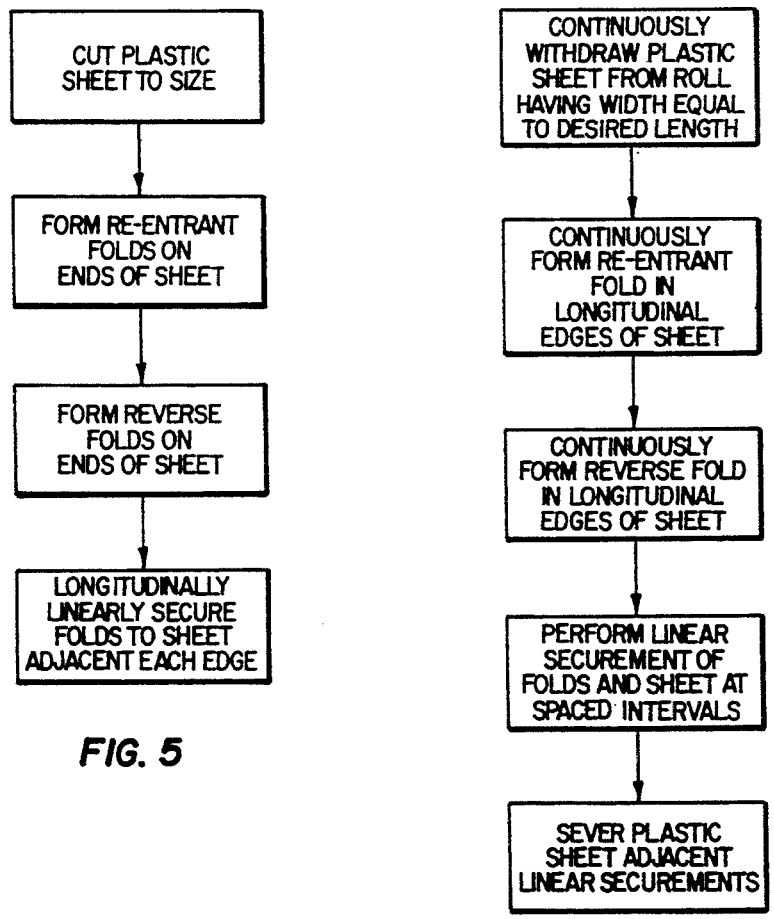
FIG. 5
FIG. 6

MEDICAL SHEET AND METHOD OF MANUFACTURE

This application is a division of application Ser. No. 07/667,424, filed Mar. 11, 1991 now U.S. Pat. No. 5,227,218.

BACKGROUND OF THE INVENTION

1. Field of the Invention

This invention relates to a protective cover sheet for isolation of the body of a patient from a support surface provided by an examination table, a hospital bed or a portable gurney, and to a method of manufacturing such cover sheet.

2. Summary of the Prior Art

Every medical doctor's office has an examining table of elongated, generally rectangular configuration upon which successive patients generally end up in a reclining position. In the same manner, hospitals and emergency vehicles are equipped with portable gurneys on which an injured or a seriously ill patient is supported for transport. Hospital beds require frequent changes of the bottom sheet. In all such cases, it is highly desirable that the patient supporting surface of the bed, examining table or the gurney, as the case may be, be protected from contact with patient bodily fluids by a cover sheet. In many cases, and particularly in doctor's offices, the cover sheet is an ordinary sheet of paper. In hospitals, the cover sheet may be formed of cloth and hence must be washed and sterilized for reuse. Similar problems may be encountered in the home due to incontinence or diarrhea.

In any case, the existence of an economical, disposable, biodegradable cover sheet that is fitted to the patient supporting surface so as to overlie all of the surface and the adjoining edges, is lacking. Moreover, in many cases, the cover sheet is highly permeable to body fluids, resulting in contamination of the patient supporting surface of the bed, examining table or gurney, requiring cleaning and sterilization of such surface.

A problem is also encountered, particularly in emergency vehicles and hospitals, in transferring the body of an injured or a seriously ill patient from the gurney to a hospital bed or operating table. With the current Aids epidemic, the personnel handling the patient are at risk by contact with the patient's bodily fluids if they physically grasp the patient. It would be highly desirable that the cover sheet be fabricated of such material as to not only be highly impermeable to body fluids but also to have sufficient tensile strength to permit the body of the patient to be lifted and moved simply by grasping the edges of the cover sheet. Lastly, the cover sheet should fit snugly on the patient supporting surface and should be disposable and biodegradable.

A cover sheet having these properties is not believed to have heretofore been disclosed in the prior art. U.S. Pat. No. 3,956,782 discusses the disadvantages of muslin sheets, but discloses a plastic cover sheet having pockets extending along each longitudinal edge that cannot be snugly fitted around the transverse ends of the patient support surface.

SUMMARY OF THE INVENTION

A cover sheet for isolation of the body of a patient from an elongated support surface of a generally rectangular configuration comprises a sheet formed of a specialized biodegradable plastic material having high tensile strength, high resistance to fluid penetration, and shaped to extend perimetrically beyond the elongated side and the end portions of the support surface. The end portions of such sheet which extend beyond the support surface are folded in such manner as to define pockets to respectively snugly surround the ends of the elongated patient support surface.

In a preferred embodiment of the invention, the pockets are formed by reversely, transversely folding the excess end portions to lie adjacent the under surface of the patient support surface. That portion of the reversely folded end portion which is intermediate the top end surface of the patient support and the reverse fold is then provided with a transverse reentrant folded portion. The total width of the re-entrant folded portion, when unfolded, is slightly greater than the thickness of the support surface for which the protective cover sheet is designed. Whether the reverse fold is formed prior to, or after the formation of the re-entrant folded portion is immaterial.

When such folded portions have been formed, they are compressed against the adjacent portions of the cover sheet and a longitudinally extending, linear securement of both folded portions to the isolation sheet is formed, either by stitching, a linear heat seal, or through the application of lines of adhesive to those portions of the plastic sheet that are to be secured together. Thus a protective sheet cover is formed having the same general dimensions as the patient support surface and having pockets formed in each end to snugly surround the cantilevered end portions of the patient support surface.

In a preferred embodiment of the invention, the pockets formed in the manner described above are then inverted before application to the patient support surface. The inversion action places those longitudinal edge portions of the sheet which are secured together within the interior of the pocket, rather than projecting exteriorly of the pocket when applied to the patient support surface. The additional advantage of inverting the pockets is that a downward bias is then imparted to the excess width portions of the protective sheet cover causing them to drape downwardly adjacent the longitudinal edges of the patient support surface. In this manner, a very neat appearance of the sheet as applied to the patient support surface is achieved.

The manufacture of a protective sheet embodying this invention can be readily accomplished by a series of manual operations on a single sheet of plastic material, or can be accomplished by an automatic operation wherein sheet plastic is withdrawn from a roll of such plastic sheet. The withdrawn plastic sheet is of a width substantially in excess of the length of the patient support surface for which the protective sheet is being manufactured. As the sheet is withdrawn, folding apparatus, of a type well known in the art, is applied to both lateral edges of the withdrawn sheet to form in such lateral edges both the reentrant fold previously described and the reverse fold.

The folded sheet then passes a securement mechanism which applies either a longitudinal stitching, a longitudinal line of adhesive, or a linear heat seal to the edges of the folded sheet to effect the linear securement of the outer ends of the folded portions to the main body of the sheet. The continuous sheet is then transversely severed adjacent the linearly secured portions to provide sheet width corresponding to that desired for the particular patient supporting surface, with each severed width having a flat configuration for packaging but having flattened tansverse pockets formed at each end for respectively snugly engaging the ends of the elongated patient support surface, particularly when the pockets are inverted.

Further advantages of the apparatus and method inventions disclosed in this application will be readily apparent to those skilled in the art from the following detailed description, taken in conjunction with the annexed sheets of drawings, on which are shown several preferred embodiments of the invention.

BRIEF DESCRIPTION OF THE DRAWINGS

FIG. 4 is an elevational view of the cover sheet prior to the folding operations indicated by dotted lines.

FIG. 5 is a schematic block diagram illustrating the steps involved in fabricating by hand a cover sheet embodying this invention.

FIG. 6 is a schematic block diagram illustrating a preferred method of fabricating a cover sheet embodying this invention by a continuous machine process.

DESCRIPTION OF PREFERRED EMBODIMENT

Figure 1:
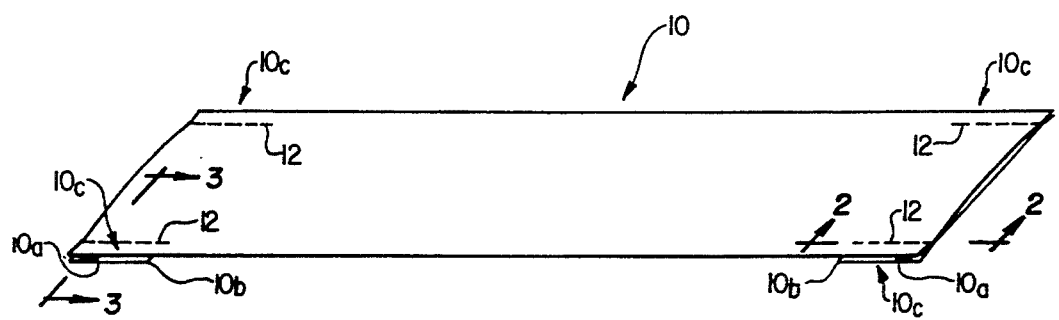
FIG. 1 is a perspective view of a cover sheet for a patient support surface as such sheet is initially formed.
Figure 2:
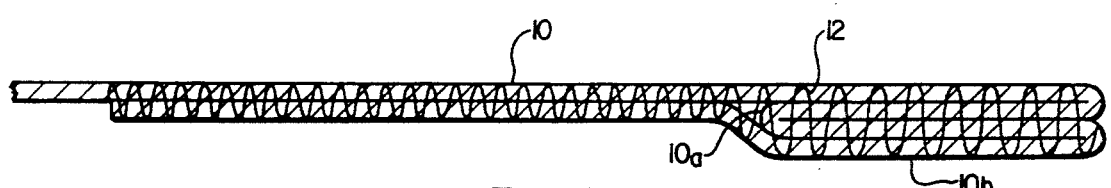
FIG. 2 is an enlarged scale sectional view taken on the plane 2—2 of FIG. 1.
Figure 3:
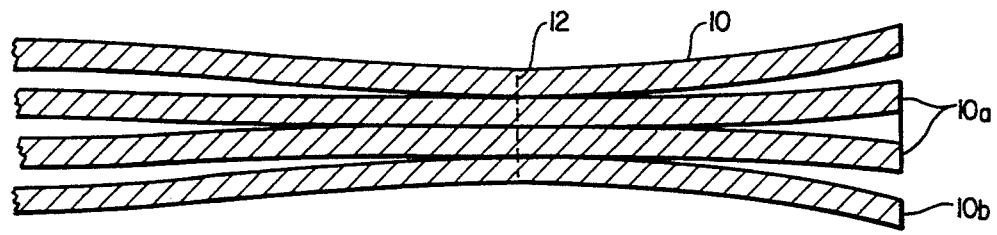
FIG. 3 is an enlarged scale partial sectional view taken on the plane 3—3 of FIG. 1.

Referring to FIG. 1, there is shown a perspective view of a protective cover sheet 10 embodying this invention in the form in which it is originally manufactured, but not in the form in which it is applied to a patient supporting surface of an examining table, bed, or gurney. As manufactured, the cover sheet 10 is of elongated rectangular construction and having a length dimension greater than the length dimension of the patient supporting surface to which it is to be applied, and, a similarly determined width dimension. Each longitudinal end of cover sheet 10 has a re-entrant folded portion 10a formed thereon. The total width of the re-entrant portion 10a, when unfolded, is substantially equal to, but not less than the thickness of the patient supporting surface. The bottom edge of each re-entrant portion 10a is reversely folded to form an end portion 10b. Both re-entrant folded portions 10a and the reversely folded end portions 10b lie snugly against the underside of the cover sheet 10 as originally manufactured, as is better shown in FIGS. 2 and 3.

Adjacent the longitudinal edges of the cover sheet 10, stitching 12 or other form of longitudinal securement is provided which effects the linear longitudinal securement of both the re-entrant portions 10a, and the reversely folded portions 10b to the main body portion of the cover sheet 10. Such linear longitudinal securement may be effected by a longitudinal heat seal, or by the application of lines of adhesive to the abuttable surfaces of the bottom surface of the cover sheet 10, the re-entrant folded portions 10a and the reversely folded portions 10b.

The width separation of the stitching 12 is slightly greater than the width of the patient support surface for which cover 10 is designed. Thus, pockets are defined on each end of the sheet which will snugly receive the ends of the patient support surface.

Referring to FIG. 4, which is a dimensional drawing, there is shown a cover sheet 10 designed for application to a patient supporting surface having a length of 72 inches and a width of 22 inches. Thus the initial length of the cover sheet 10 is preferably approximately 90 inches in length. Assuming that the thickness of the patient supporting surface is 4 inches, the reversely folded portions 10a are each 2 inches in width, given a total unfolded width of 4 inches. The reversely folded portion 10b may be of any convenient length, preferably greater than that of the re-entrant folded portions 10a and here shown as being 5½ inches. The width of the cover sheet 10 is approximately 8 inches greater than the patient supporting surface to which it is to be applied.

The locations of the folds which form the re-entrant folded portion 10a and the reversely folded portion 10b are indicated by the transverse dotted lines.

Figure 7:
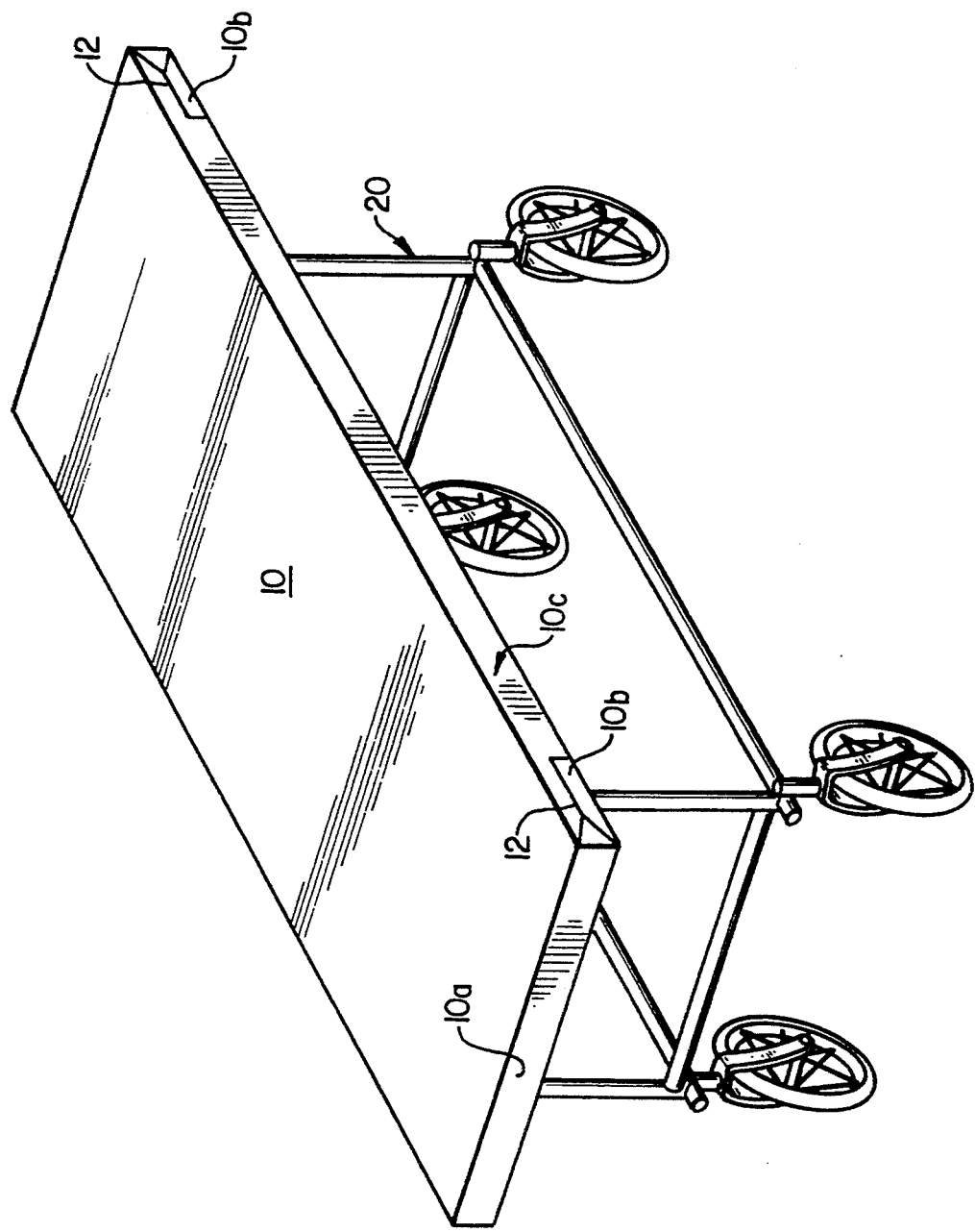
FIG. 7 is a perspective view of the cover sheet embodying this invention when the end portions thereof are inverted and the cover is applied to a patient supporting surface.

Referring now to FIG. 7, the cover sheet 10 is shown as applied to the patient supporting surface (not shown) of a portable gurney 20. Before applying the cover sheet 10 to the patient supporting surface, both of the folded ends are inverted, thus placing the tabs 10c, which extend laterally beyond the stitching 12 or other form of longitudinal securement illustrated in FIG. 1, within the confines of the respective folded end portion which then defines a pocket to snugly receive the respective end portion of the patient supporting surface of the gurney 20.

The cover sheet 10 is preferably formed from a plastic material having both high tensile strength and high resistance to fluid permeation. A plastic sheet having these properties, yet being economical enough to warrant use as a disposable cover sheet comprises a polypropylene sheet formed by the so-called spun bonded process wherein a plurality of polpropylene fibers are laid on a mat and then heated and compressed to form a substantially impervious sheet. This type of sheet is known in the art and may be obtained from a number of suppliers of polypropylene sheet. A preferred density or weight of such sheet is in the range of 1.25 to 2.00 ounces per square yard. Preferably, a sheet having a weight of about 1.6 ounces per square yard is employed. This sheet has a grab tensile resistance in the machine direction of 107.8 lbs. and in the cross direction, 58.8 lbs. It's grab elongation in the machine direction is 43.6% and in the cross direction 53.1%. No chemical binders are employed in the fabrication of such sheet. Its strength is in no manner affected by contact with fluids and it is highly resistant to fluid permeation.

A sheet having these properties has sufficient strength that an average size patient lying on the sheet may be bodily lifted by merely grasping the edges of the sheet, eliminating any contact with the body of the patient.

Referring now to FIGS. 5 and 6, there is indicated by block diagrams two methods of forming a cover sheet embodying this invention. The first method illustrated by the blocks in FIG. 5 has already been described.

A preferred method for producing large quantities of covers by a substantially continuous process is illustrated by the block diagram of FIG. 6. In this method, the polypropylene sheet is obtained on rolls having a width equal to the desired length of the sheet for application to a particular patient supporting surface. Thus, using the example of FIG. 4, the width of the continuous sheet on the roll would be 90 inches and this large width sheet is continuously withdrawn from the roll.

Due to the fact that the longitudinal edges of this wide sheet will become the transverse edges of the cover sheet, the re-entrant fold and the reverse folds may be continuously formed in the longitudinal edges of the wide sheet. Such folding operations are performed by apparatus that is entirely conventional in the art.

Having achieved the two folding operations, and effecting the flattening of the folded portions of the sheets, the sheet is then passed through two seaming apparatuses respectively located at each side of the wide sheet. These seaming apparatuses are well known in the art and are synchronously operated with the movement of the sheet to produce the seams 12 shown in FIG. 1.

After the seams 12 have been produced, conventional cutting apparatus is employed to cut the wide sheet transversely to produce a sheet form 10 identical to that shown in FIG. 1. Obviously, the cutting is performed outside of each of the seams 12.

With the aforedescribed method, cover sheets may be continuously and automatically produced, thus greatly reducing the manufacturing costs of such sheets and making the sheets very attractive to hospitals and doctors as a biodegradable, disposable item.

Those skilled in the art will recognize that the cover sheet construction, and the methods of fabricating same heretofore described, represent a significant advance in the field of protective covers for any patient supporting surface. Obviously, cover sheets may be made in larger configurations so as to fit hospital beds and beds employed in the home. In the latter case, illnesses such as incontinence and diarrhea may makes the employment of a substantially fluid impermeable sheet highly desirable to protect the mattress upon which the patient is resting.

What is claimed and desired to be secured by Letters Patent is:

1. A patient support apparatus for use with a patient support surface comprising:
    a sheet being fabricated from spun bonded polypropylene and originally sized and shaped to extend at least to a perimeter of the patient support surface;
    the sheet having high resistance to fluid penetration in order to protect the patient support surface from contact from bodily fluids of a patient;
    the sheet further having high tensile strength to allow lifting of the patient by grasping edges of the sheet; and
    the sheet further includes end pocket portions for snugly receiving the transverse end portions of the patient support surface.

2. The apparatus of claim 1 wherein the pockets are formed from end portions of the sheet reversely folded to form reverse folds, each reverse fold having lateral edge portions secured to an adjacent sheet portion by longitudinal seams.

* * * * *